(12) United States Patent
Howard et al.

(10) Patent No.: US 8,357,398 B2
(45) Date of Patent: Jan. 22, 2013

(54) BENZONATATE COMPOSITIONS AND METHODS OF USE

(75) Inventors: William Wayne Howard, Morristown, NJ (US); Russell Francis Somma, Sparta, NJ (US); Doreen Marie Frank, Lebenon, NJ (US)

(73) Assignee: Alitair Pharmaceuticals Inc., Morris Plains, NJ (US)

( * ) Notice: Subject to any disclaimer, the term of this patent is extended or adjusted under 35 U.S.C. 154(b) by 0 days.

(21) Appl. No.: 12/925,353

(22) Filed: Oct. 20, 2010

(65) Prior Publication Data

US 2011/0091509 A1   Apr. 21, 2011

Related U.S. Application Data

(60) Provisional application No. 61/279,470, filed on Oct. 21, 2009.

(51) Int. Cl.
| | |
|---|---|
| *A61K 9/14* | (2006.01) |
| *A61K 9/20* | (2006.01) |
| *A61K 9/54* | (2006.01) |
| *A61K 31/075* | (2006.01) |
| *A61K 31/245* | (2006.01) |
| *B01J 45/00* | (2006.01) |

(52) U.S. Cl. ........ 424/483; 424/465; 424/501; 514/538; 514/544; 514/716; 514/717; 514/718; 521/30

(58) Field of Classification Search .......... None
See application file for complete search history.

(56) References Cited

U.S. PATENT DOCUMENTS

| | | | | |
|---|---|---|---|---|
| 4,775,694 A | | 10/1988 | Press et al. ............... 514/535 |
| 5,032,393 A | * | 7/1991 | Douglas et al. ............ 424/78.13 |
| 5,846,557 A | | 12/1998 | Eisenstadt et al. .......... 424/439 |
| 6,001,392 A | * | 12/1999 | Wen et al. ................ 424/486 |
| 6,569,463 B2 | * | 5/2003 | Patel et al. .............. 424/497 |
| 6,608,073 B1 | | 8/2003 | Hossain et al. ............ 514/277 |
| 6,793,934 B1 | | 9/2004 | Burnside et al. .......... 424/464 |
| 6,969,508 B2 | | 11/2005 | Dugger, III .............. 424/45 |
| 7,067,116 B1 | * | 6/2006 | Bess et al. ............... 424/78.1 |
| 7,407,669 B2 | | 8/2008 | Leung et al. ............. 424/443 |
| 7,648,712 B2 | | 1/2010 | Bess et al. ............... 424/407 |
| 2004/0126324 A1 | * | 7/2004 | Hughes .................. 424/10.1 |

OTHER PUBLICATIONS

Singh et al. (FABAD J. Pharm. Sci. 2007, 32, 91-100).*
Borodkin et al. (J. Pharm. Sci. 1971, 60(10), 1527).*
Borodkin et al. (J. Pharm Sci. 1970, 59(4), 481-486).*
Jeong et al. (J. Pharm. Sci. 2007, 96, 3, 618-632).*
Barr Laboratories Inc., "Benzonatate—benzonatate capsule", Aug. 2007.
Rohm and Haas Co., "Amberlite™IRP 64 Pharmaceutical Grade Cation Exchange Resin", Feb. 2006.
Bajpai S K et al., "Ion exchange resins in drug delivery", . In *Ion Exchange and Solvent Extraction, A Series of Advances*, 18, CRC Press, 2007.
Hughes, Lyn, "Ion Exhange Resins, Unique Solutions to Formulation Problems", Pharmaceutical Technology, Excipients & Dolid Dosage Forms 2004, p. 20-25, www.pharmtech.com.
Harland, C.E., "Ion Exchange Theory and Practice" Second Edition, p. 1-3, The Royal Society of Chemistry, 1994.
Elder, David P., "Pharmaceutical Applications of Ion-Exchange Resins", J. Chem. Education, vol. 83, No. 4, 575-587, Apr. 2005.
Singh, inderbit et al., "Ion Exchange Resins: Drug Delivery and Therapeutic Applications", J. Pharm. Sci., 32, 91-106 2007.

* cited by examiner

*Primary Examiner* — Ernst Arnold
(74) *Attorney, Agent, or Firm* — Shelson Kavesh

(57) ABSTRACT

Oral dosage forms of benzonatate useful for anti-tussive and anti-tussive/combination applications.

10 Claims, 11 Drawing Sheets

Figure 1 Effects of Resinates on Simulated Buccal Exposure of Benzonatate
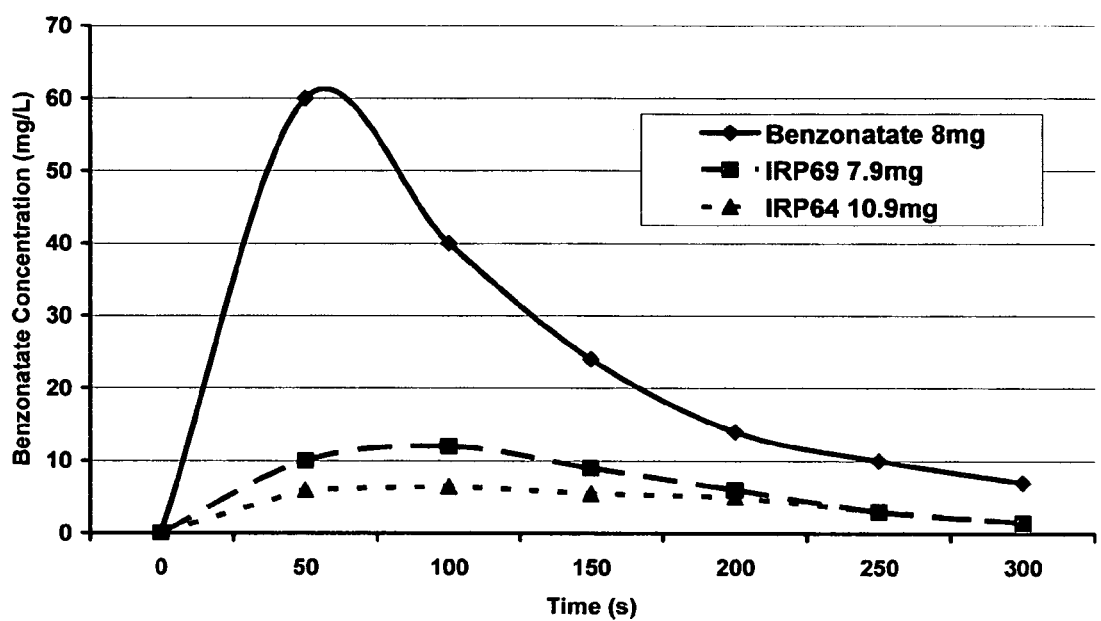

Figure 2 Resination of the Active Ingredient, Intermediate:
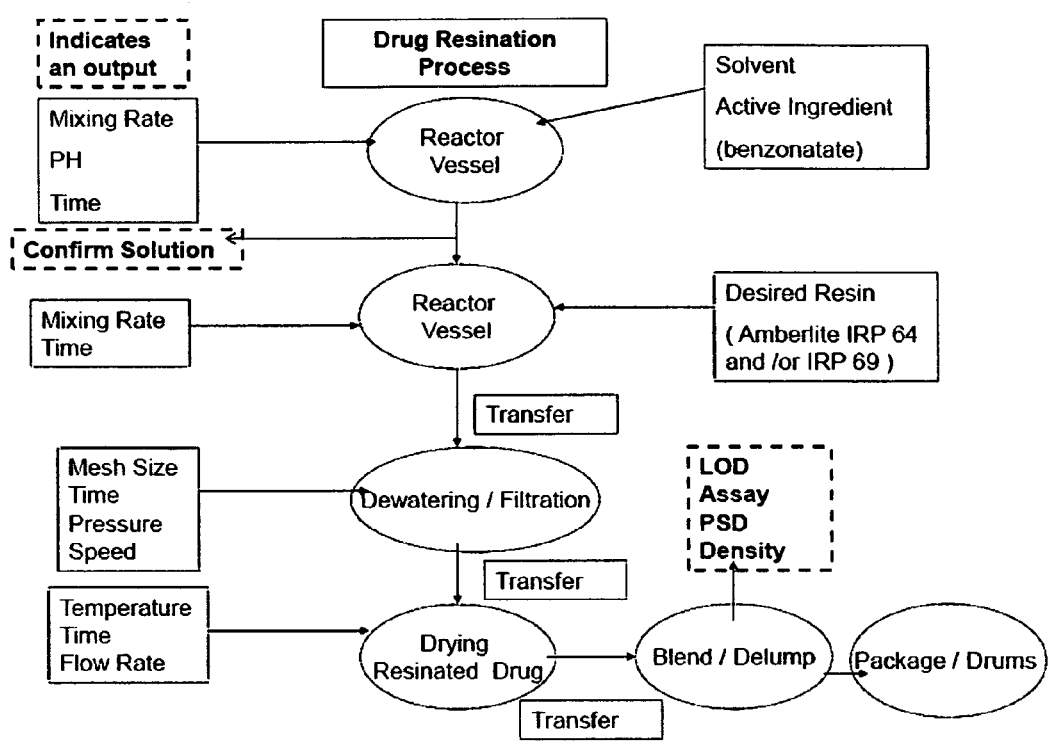

Figure 3_IR Resin Coating, Intermediate
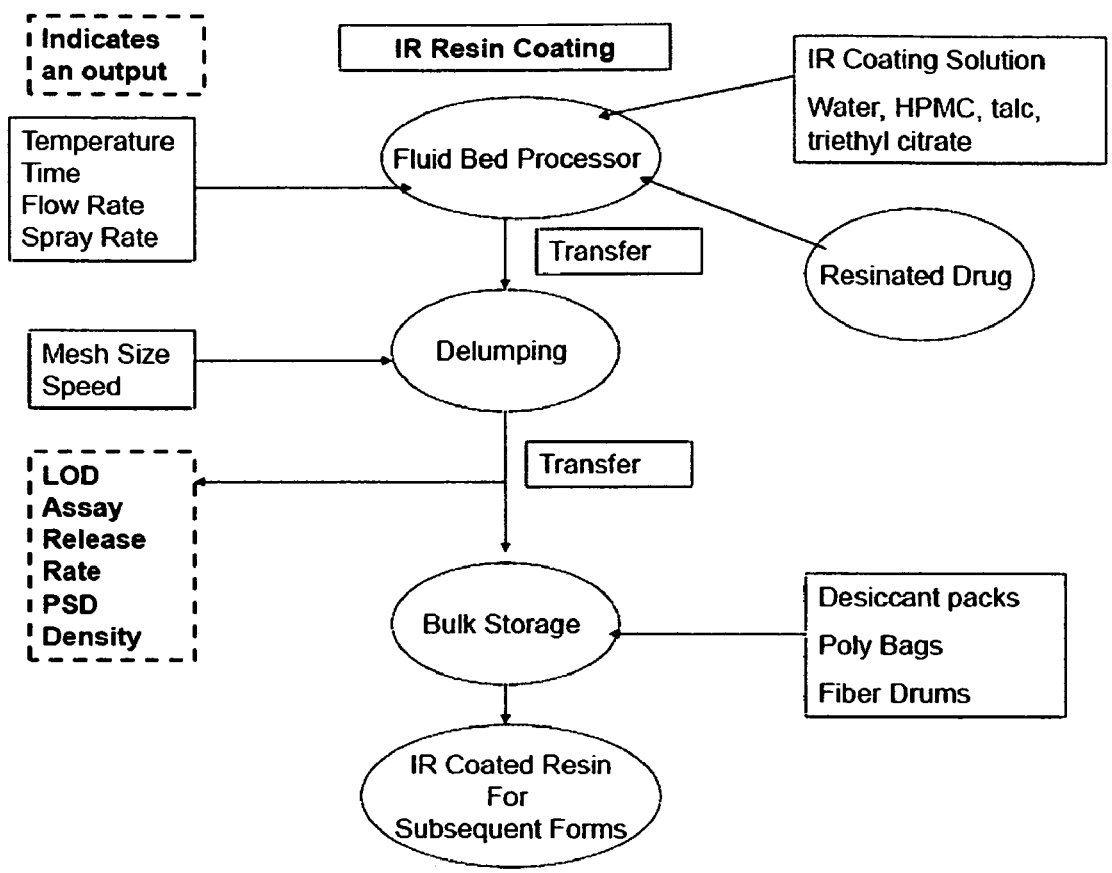

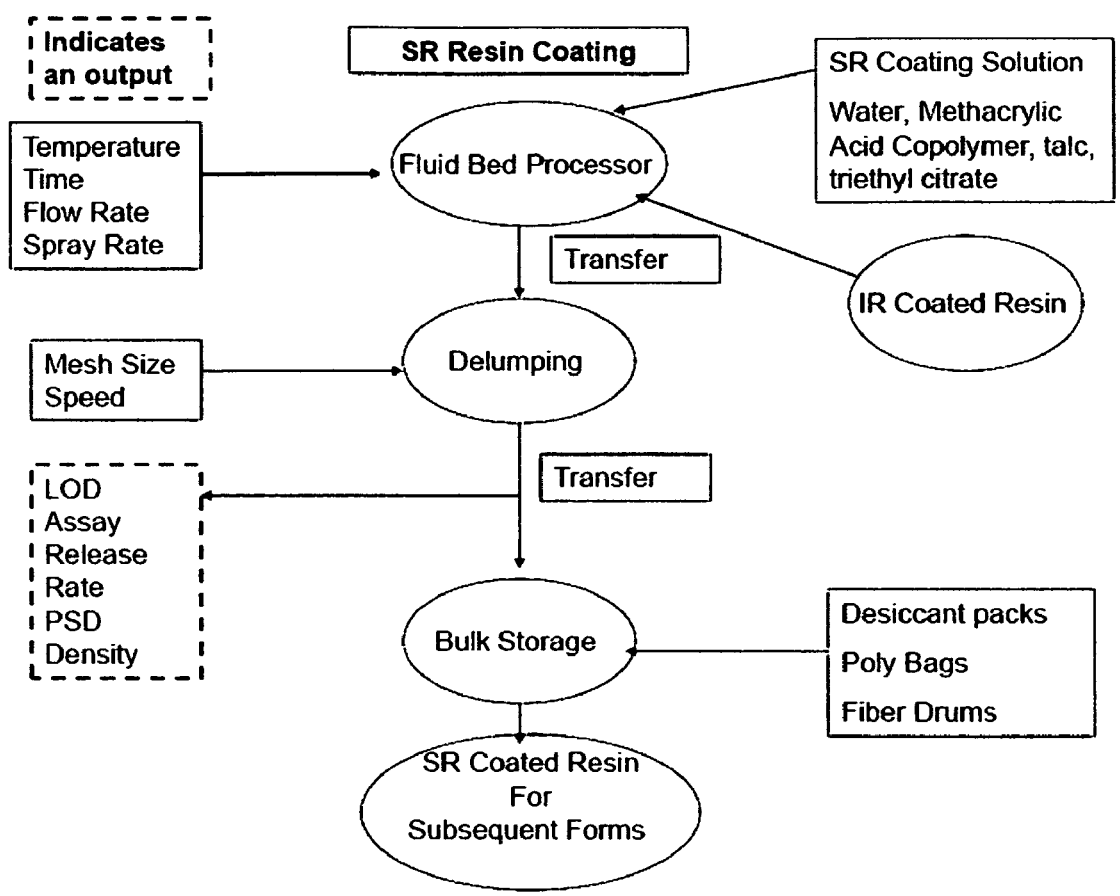
Figure 4 SR Resin Coating, Intermediate

Figure 5 Fixed Combination Second Medicinal Component, Intermediate
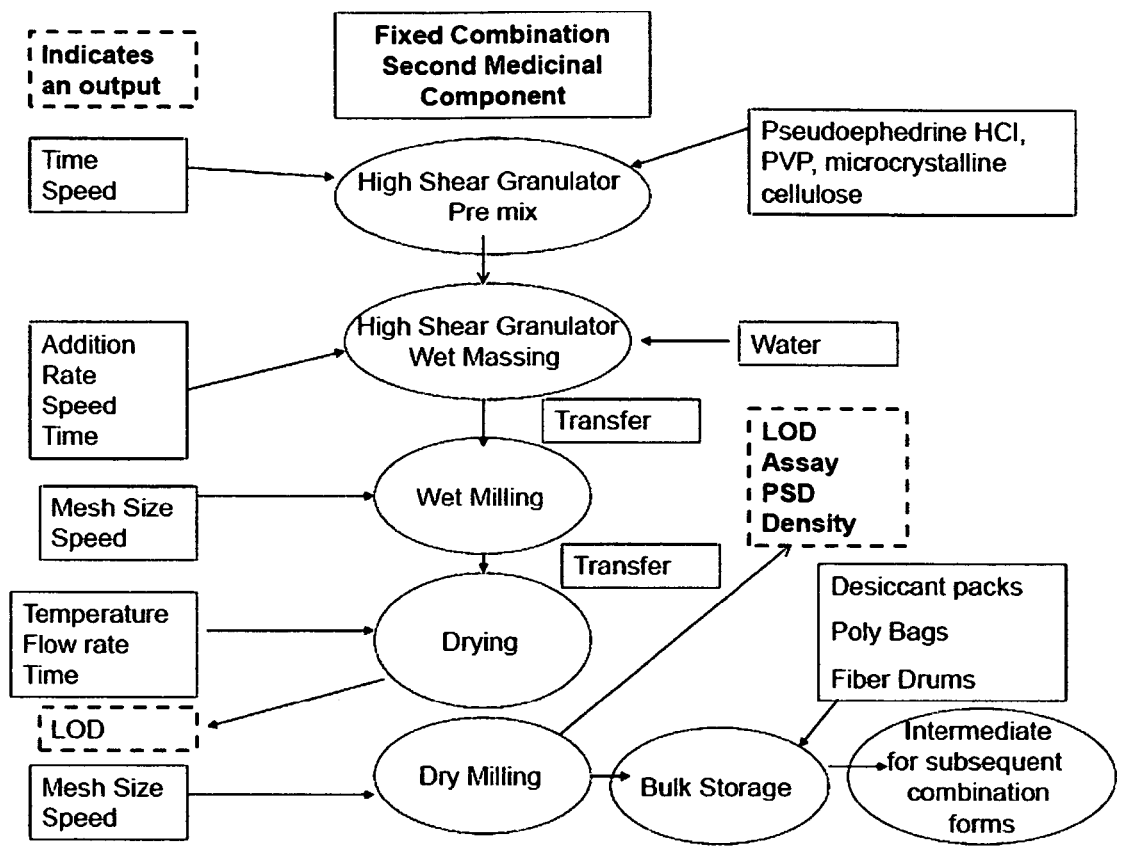

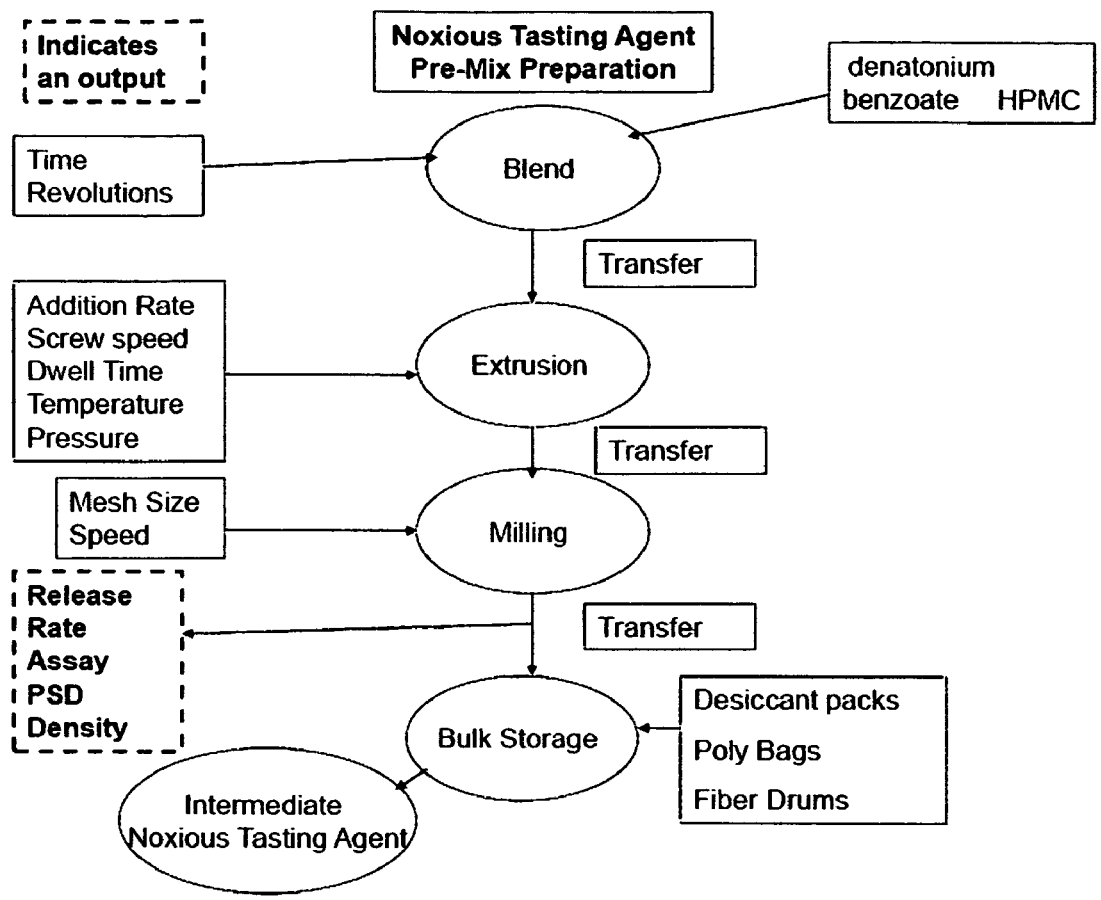
Figure 6 Noxious Tasting Agent Pre-Mix, Intermediate

Figure 7 IR Mono-Substance Oral Solid Dosage Form, Hard Gelatin Capsule
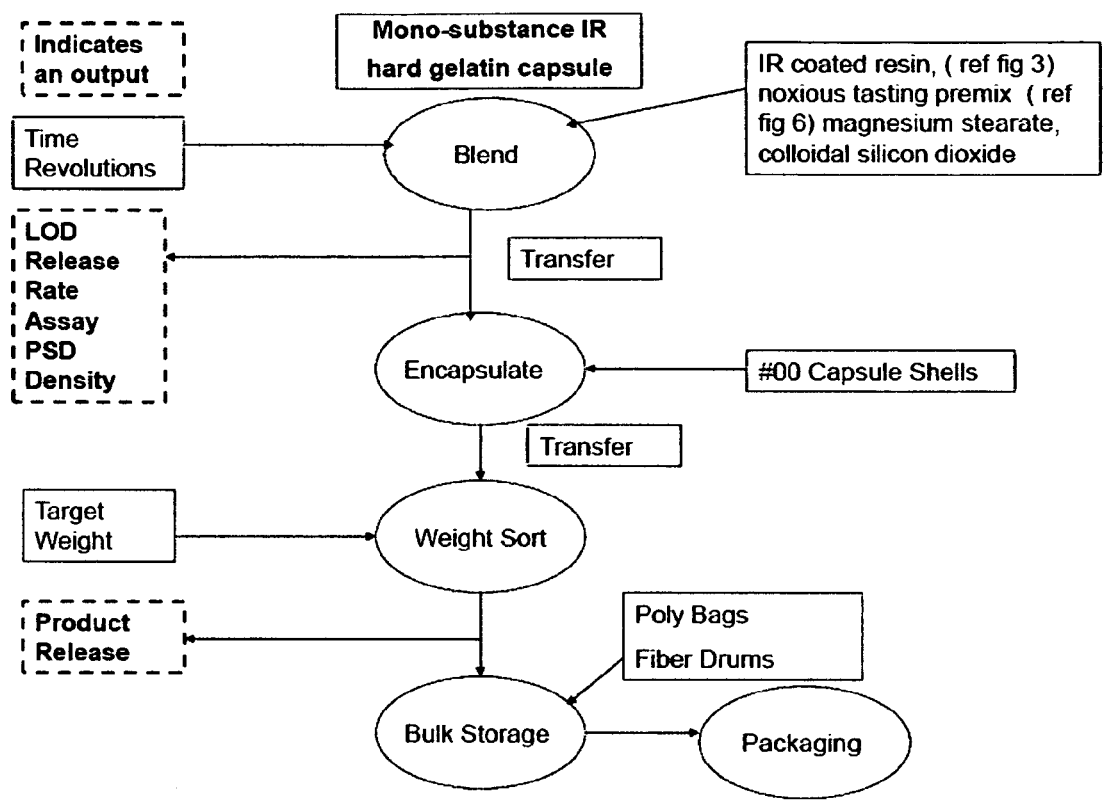

Figure 8 IR Mono-Substance Oral Solid Dosage Form Compressed Tablet
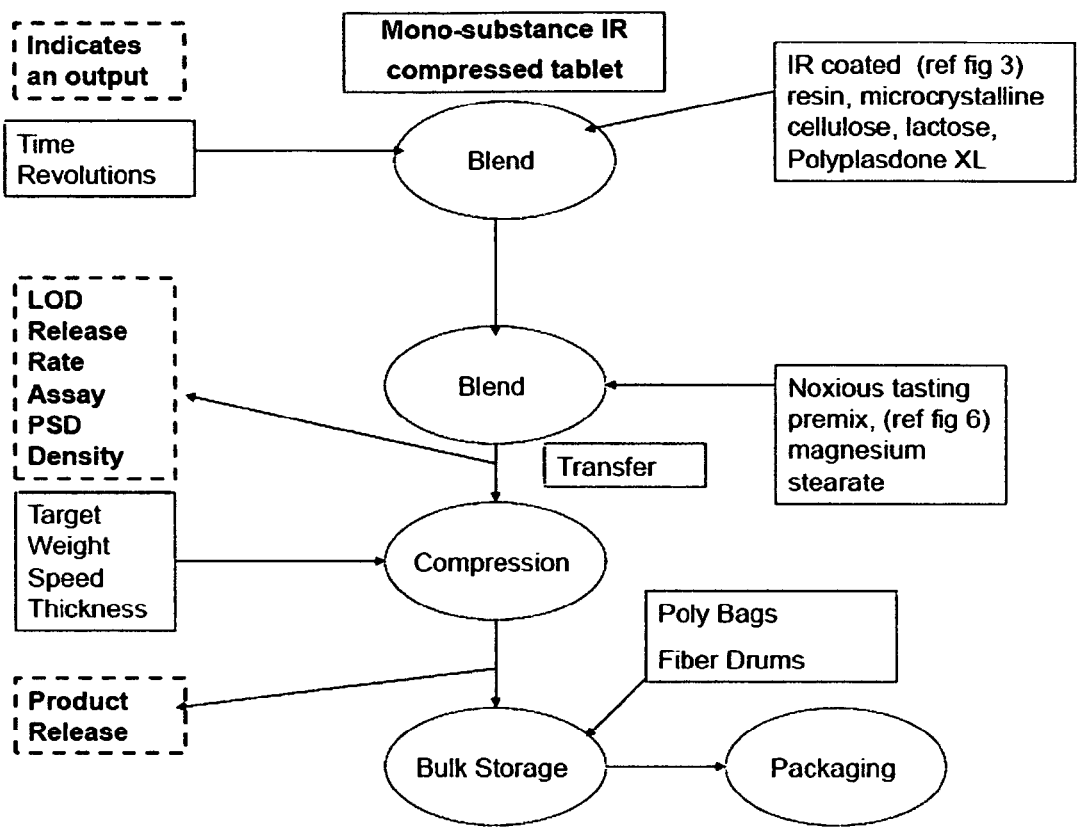

Figure 9 Fixed Combination using the IR resin, Compressed Tablet
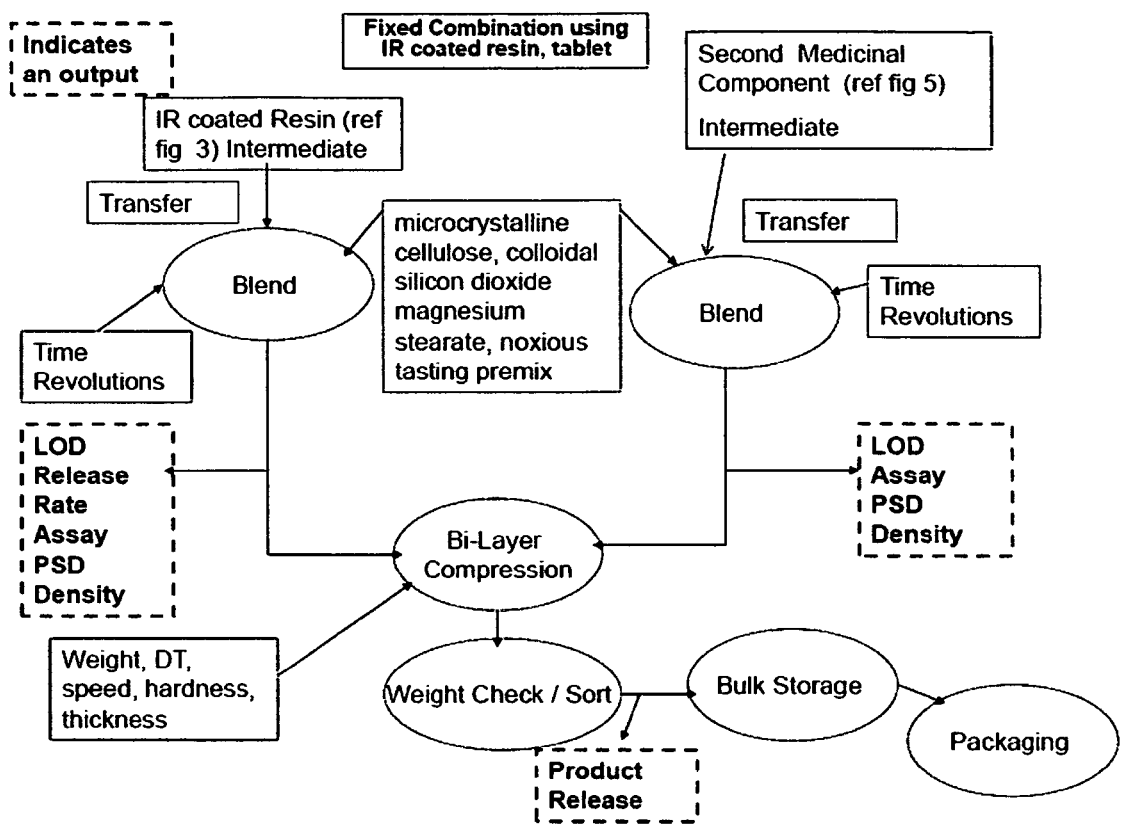

Figure 10 Fixed Combination using the IR resin Hard Gelatin Capsule
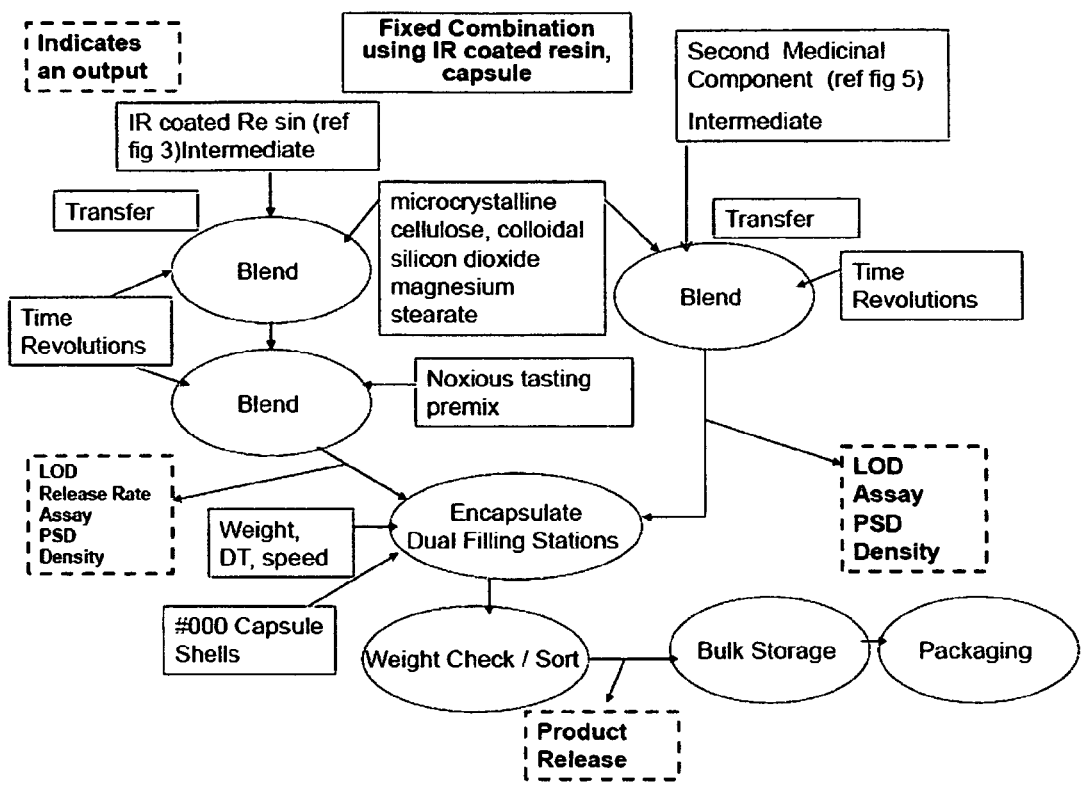

Figure 11 Sustained Release Mono Substance Hard Gelatin Capsule
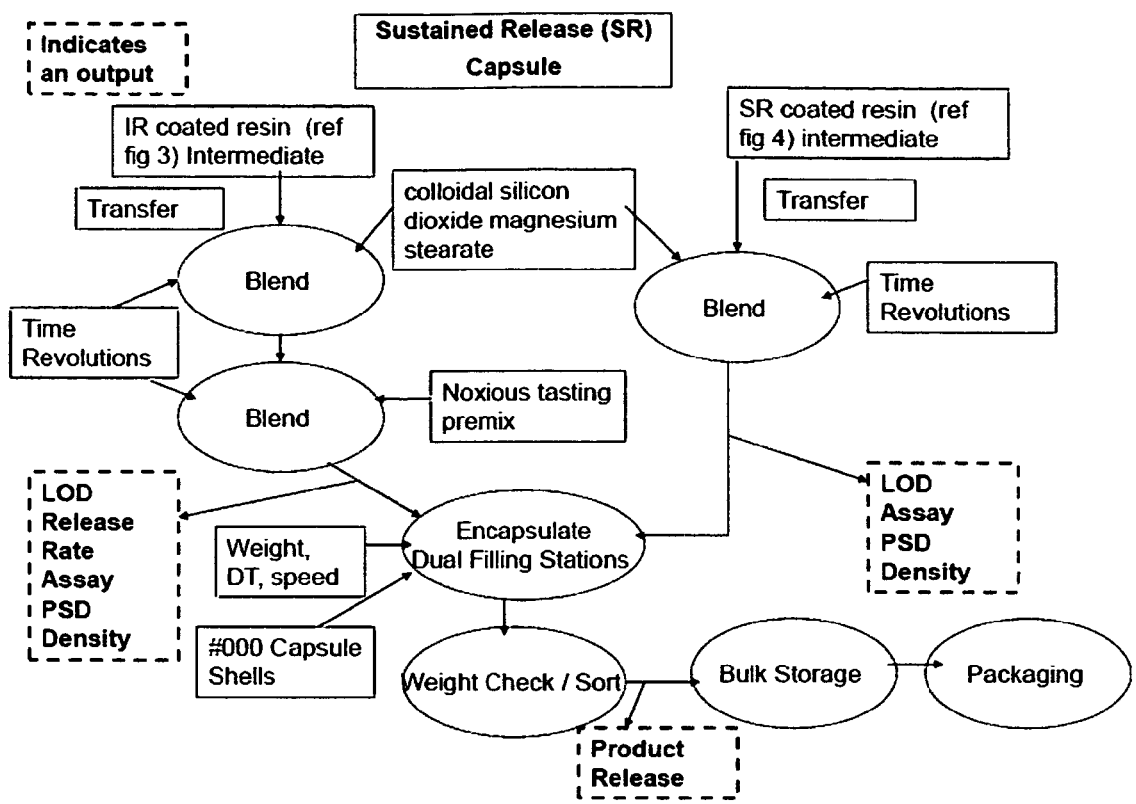

BENZONATATE COMPOSITIONS AND METHODS OF USE

CROSS-REFERENCE TO RELATED APPLICATIONS

This application claims the benefit of U.S. Provisional Application 61/279,470 filed Oct. 21, 2009. It is related to pending application Ser. No. 12/799,259 filed Apr. 21, 2010 and to pending application Ser. No. 12/807,434 filed Sep. 3, 2010.

BACKGROUND OF THE INVENTION

1. Field of the Invention

The invention relates to oral dosage forms of benzonatate useful for anti-tussive and anti-tussive/combination applications.

2. Description of the Related Art

Benzonatate is a non-narcotic oral antitussive (cough suppressant) drug that works by anesthetizing the tissues of the lungs and pleura responsible for the cough reflex. Benzonatate is chemically related to anesthetic agents of the para-aminobenzoic acid class (e.g., procaine; tetracaine). Benzonatate anesthetizes the stretch receptors in the respiratory passages, reducing the cough reflex. As a non-narcotic with little or no abuse potential, benzonatate is a useful drug for treating cough. Further, benzonatate does not have many of the serious side effects that narcotic cough compounds such as codeine and hydrocodone have which include:

Narcotic Side Effects
Overdose, respiratory depression
Drug interactions
    Alcohol, minor tranquilizers, other CNS drugs
Constipation, sedation
Abuse/dependence
Psycho/motor effects Due to these side effects, many patients cannot take narcotic cough products:

Pain patients, abuse history, elderly, young children, COPD patients, critically ill, military/police/fire/health transportation workers, pregnant & post-partum women In spite of the many reasons to use non-narcotic cough preparations, current formulations of benzonatate have a serious safety issue that can offset its benefits as a non-narcotic alternative to codeine and hydrocodone. Current formulations of benzonatate, if released in the mouth through dissolution, either by contact with saliva or aided by chewing or sucking, can rapidly cause oropharyngeal anesthesia that may lead to adverse events including choking.

Benzonatate has a secondary pharmacologic effect as a local anesthetic. If the drug is released in the oral cavity serious adverse effects can occur. In the Tessalon prescription drug label, the Signs and Symptoms section states:

"If capsules are chewed or dissolved in the mouth, oropharyngeal anesthesia will develop rapidly. CNS stimulation may cause restlessness and tremors which may proceed to clonic convulsions followed by profound CNS depression".

The formulations of the invention preserve the advantages of benzonatate while eliminating or diminishing hazards of its use. The inventive formulations of benzonatate use ion exchange resin technology to diminish or eliminate the choking hazard and adverse events if the product is released in the oral mucosa. It is believed that the use of ion exchange resins to create benzonatate compositions that can reduce or eliminate the choking and adverse effects associated with current formulations of benzonatate has not been previously disclosed. A review of the ion exchange literature and patents revealed the following pharmaceutical uses of ion-exchange resins:

Reduce Food Effects on Pharmacokinetic Release Rates
Taste Masking
Disintegrant/Superdisintegrant
Improved Dissolution
Powder Processing Aid
Drug Stabilization
Oral modified release formulations: Sustained Release, Controlled Release No patent or reference source reviewed mentioned the use of ion-exchange for preventing release of a drug in the oral cavity. Further, no source revealed the use of denatonium benzoate or similar noxious tasting agent to prevent patients from chewing or sucking a benzonatate capsule or tablet.

Surprisingly and unexpectedly, benzonatate could be resinated with both a strong acid resin (IRP69) and a weak acid resin (IRP64) with significant loadings in excess of 40%.

SUMMARY OF THE INVENTION

Benzonatate is a butyl amine having the following chemical structure:

[Chemical structure diagram]

Pharmaceutical grade benzonatate is a mixture of homologues wherein the number of ethylene oxide units varies. It will be understood that the benzonatate employed in the invention is a mixture of homologues meeting the benzonatate specifications of the United States Pharmacopeia of 2005, i.e., USP28.

In a first embodiment, the invention is a pharmaceutical composition comprising benzonatate bound to at least one ion exchange resin.

In a second embodiment, the invention is a pharmaceutical composition comprising (i) benzonatate bound to a member of the group consisting of a weak acid ion exchange resin, a strong acid ion exchange resin and their combination.

In a third embodiment, the invention is a pharmaceutical composition comprising (i) benzonatate bound to an ion exchange resin, and, ii) at least one additional pharmaceutically active agent.

In a fourth embodiment, the invention is a pharmaceutical composition comprising benzonatate and at least one additional pharmaceutically active agent bound to at least one ion exchange agent.

In a fifth embodiment, the invention is a pharmaceutical composition comprising (i) benzonatate bound to an ion exchange resin and (ii) a noxious tasting agent.

The invention also includes a method of treating a cough while reducing or preventing adverse effects caused by a release of benzonatate into the oral cavity comprising treating a patient with a pharmaceutical composition of the invention.

BRIEF DESCRIPTION OF THE DRAWINGS

FIG. 1 is a chart that illustrates the comparative buccal release of bound and unbound benzonatate.

FIG. 2 is a flow chart that illustrates a process for resination of the active Ingredient forming a drug resinate.

FIG. 3 is a flow chart that illustrates a process for adding an immediate release (IR) resin coating to the drug resinate.

FIG. 4 is a flow chart that illustrates a process for adding an extended release (SR) resin coating to the drug resinate.

FIG. 5 is a flow chart that illustrates a process for forming a second medicinal component intermediate.

FIG. 6 is a flow chart illustrating a process for forming a noxious tasting agent intermediate FIG. 7 is a flow chart illustrating the formation of a mono substance IR solid dosage form hard gelatin capsule.

FIG. 8 is a flow chart illustrating the formation of a mono substance IR solid dosage form compressed tablet.

FIG. 9 is a flow chart illustrating the formation of a fixed combination pharmaceutical using the IR resin compressed tablet.

FIG. 10 is a flow chart illustrating the formation of a fixed combination pharmaceutical using the IR resin hard gelatin capsule.

FIG. 11 is a flow chart illustrating the formation of an extended release mono substance pharmaceutical hard gelatin capsule.

DETAILED DESCRIPTION OF THE INVENTION

In a first embodiment, the invention is a pharmaceutical composition comprising benzonatate bound to at least one ion exchange resin.

In a second embodiment, the invention is a pharmaceutical composition comprising benzonatate bound to a member of the group consisting of a weak acid ion exchange, a strong acid ion exchange resin and their combination.

In a third embodiment, the invention is a pharmaceutical composition comprising (i) benzonatate bound to an ion exchange resin, and, ii) at least one additional pharmaceutically active agent.

The inventive formulations of benzonatate use ion exchange resin technology to diminish or eliminate the choking hazard and adverse events if the product is released in the oral mucosa.

The inventive formulations can use weak acid resins, strong acid resins or both weak acid resins and strong acid resins as part of the formulation with or without a noxious tasting agent. The inventive formulations can be either immediate release or extended release formulations or both in one medicament.

Strong acid resins are so named because their chemical behavior is similar to strong acids. During the process of creating the resin polymer, a strong acid such as $SO_3H$ is introduced into the resin. This sulfonic acid group is very highly ionizable and thus produces many ions available for the exchange process during drug resination.

In a weak acid resin the ionizable group introduced to the polymer is a carboxylic acid (COOH) as opposed to the sulfonic acid group ($SO_3H$) used in strong acid resins. These resins behave similarly to weak organic acids so are weakly dissociated i.e. have fewer ions available for exchange.

An acid dissociation constant, $pK_a$, (also known as acidity constant, or acid-ionization constant) is a quantitative measure of the strength of an acid in solution. The larger the value of $pK_a$, the smaller the extent of dissociation. A strong acid such as $SO_3H$ pKa is approximately 0. A weak acid such COOH has pKa in the range of 4.0 to 7.0.

AMBERLITE IRP69 manufactured by DOW Chemicals is thought to have a $pK_a$ value of less than 1 so is a strong acid resin.

AMBERLITE IRP64 (CAS Registry No. 80892-32-6) is thought to have $pK_a$ value of greater than 4 so is a weak acid resin.

The immediate and extended release capsule products described here are a multi-particulate system composed of benzonatate bound to ion exchange resin particles that improves the safety profile of benzonatate as currently marketed and therefore increase its usefulness in the treatment of cough.

Ion exchange is a reversible chemical reaction wherein an ion (an atom or molecule that has lost or gained an electron and thus acquired an electrical charge) from solution is exchanged for a similarly charged ion attached to an immobile solid particle.

An ion-exchange resin is an insoluble matrix (or support structure) normally in the form of small (1-2 mm diameter) beads, usually white or yellowish, fabricated from an organic polymer substrate. The material has a highly developed structure of pores on the surface of which are sites which easily trap and release ions. The trapping of ions takes place only with simultaneous releasing of other ions; thus the process is called ion-exchange.

These solid ion exchange particles are either naturally occurring inorganic zeolites or synthetically produced organic resins. The synthetic organic resins are the predominant type used today because their characteristics can be tailored to specific applications.

Ion exchange resins are classified as cation exchangers, that have positively charged mobile ions available for exchange, and anion exchangers, whose exchangeable ions are negatively charged. Both anion and cation resins are produced from the same basic organic polymers. They differ in the ionizable group attached to the hydrocarbon network. It is this functional group that determines the chemical behavior of the resin. Resins can be broadly classified as strong or weak acid cation exchangers or strong or weak base anion exchangers.

The benzonatate resin complex is achieved by an ionic binding of the benzonatate molecule to the resin bead. The benzonatate molecule will only disassociate from the resin in the presence of an acidic environment and/or a strong electrolyte solution e.g. NaCl, both of which are found in the stomach. In the oral cavity, saliva is normally alkaline, with a pH of 7.2 or above. In addition the oral cavity has a low concentration of strong ionic species such as NaCl. As noted, an acidic environment and/or a strong electrolyte solution are necessary for the benzonatate molecules to disassociate from the resinate beads. Because the ion exchange process is stoichiometric, the small number of available ions means that few benzonatate ions can be released into the oral cavity. Therefore, one would not expect significant disassociation of the resin complex in the oral cavity as compared to the gastric environment. Additionally, simple mechanical forces, such as created by chewing or sucking, will not cause the benzonatate molecules to disassociate from the resinate beads. Only a chemical process in an acidic environment and/or the presence of strong ionic species can cause such a disassociation. Therefore, a formulation of benzonatate with a weak or strong acid resin significantly diminishes or entirely eliminates the hazards associated with benzonatate being released into the oral mucosa. The addition of denatonium benzoate or similar noxious tasting agent further decreases the tendency for a patient to chew or suck a benzonatate tablet or capsule.

The inventive formulations provide a significant safety benefit in the use of benzonatate for cough relief by reducing or eliminating the choking hazard associated with current benzonatate formulations.

The pharmaceutical compositions of the invention are characterized as safer to use by patients because the ion exchange resins will release little if any of the benzonatate into the oral cavity should the tablet or capsule is chewed. Optionally, a noxious tasting agent may be included in the formulation to deter chewing or sucking of the tablet or capsule.

In another embodiment, the invention is a pharmaceutical composition comprising (i) benzonatate bound to an ion exchange resin and (ii) a noxious tasting agent.

A noxious tasting agent such as denatonium benzoate has an extremely bitter taste and should the patient chew the product, a very unpleasant taste is created in the oral cavity. This may cause the patient to cease chewing or sucking the medicament and may cause a reflexive expectoration of the medicament. The noxious tasting agent can be, for example, denatonium benzoate, cayenne pepper or capsaicin.

The pharmaceutical composition can be formulated, for example, as a capsule or compressed tablet. The inventive compositions are preferably in a solid oral dosage form, such as a tablet, caplet or capsule containing benzonatate bound to an ion exchange resin and, optionally, a noxious tasting agent added to further deter chewing or sucking on the solid oral dosage form.

Furthermore, the invention includes compositions including both an immediate release (IR) component and extended release (ER) component.

Weak acid ion exchange resins useful in the invention include, for example, Amberlite IRP64, DOWEX MAC-3, but other weak acid ion exchange agents may be used. Strong acid resin include, for example, Amberlite IRP69, DOWEX 88, or DOWEX 50WX8.

The pharmaceutical composition can optionally include a second ion exchange resin. This second ion exchange resin is bound to one or more pharmaceutical agents and can be coated with a extended release coating, resulting in extended release of the pharmaceutically active agent(s) from the second ion exchange resin when administered to a patient.

By "pharmaceutically active agent" is meant agents other than food articles that are intended to diagnose, cure, mitigate, treat or prevent disease in man or other animals or that are intended to affect the structure or any function of the body of man or other animals that are physiologically acceptable. The agent could be a combination of drug therapies as well as a single agent.

By "noxious tasting agent" is meant an agent that, when released into the oral cavity is bitter, foul tasting, pepper like or any other agent that is otherwise safe and physiologically acceptable but has a very bad taste.

By "physiologically acceptable" is meant those substances that are adequately tolerated without causing unacceptable negative side effects.

By "ion exchange resin" is meant an insoluble solid matrix that carries exchangeable ions with either a positive or negative charge. The trapping of ions takes place only with simultaneous releasing of other ions. Ions are exchanged in stoichiometrically equivalent amounts of other ions with the same electrical charge when the ion exchange material is in contact with an electrolyte solution.

By "resinate" is meant the complex formed when a drug exchanges an ion with a resin particle in the stoichiometric process described above and a drug/resin complex is formed.

By "weak acid ion exchange resin" is meant in a weak acid resin the ionizable group introduced to the polymer is a carboxylic acid (COOH) as opposed to the sulfonic acid group ($SO_3H$) used in strong acid resins. These resins behave similarly to weak organic acids so are weakly dissociated i.e. have fewer ions available for exchange.

By "strong acid ion exchange resin" is meant in a strong acid resin the ionizable group introduced to the polymer is a sulfonic acid group ($SO_3H$) as opposed to the carboxylic acid (COOH) used in weak acid resins. These resins behave similarly to strong organic acids so are strongly dissociated i.e. have many ions available for exchange.

By "immediate release" is meant that the pharmacologically active agent is released from the formulation immediately such that 80%, 85%, 90%, or even 95% of the pharmaceutically active agent in the formulation is released within 45 minutes when dissolution is measured according to the USP 31 NF 26 section 711.

By "extended release" is meant that the pharmaceutically active agent is released from the formulation at a controlled rate such that the formulation allows for a reduction in dosing frequency as compared to that presented by a conventional dosage form, e.g. an immediate release dosage form.

Noxious Tasting Agents

The drug-containing ion exchange resins of the invention may be also formulated with noxious tasting agents. These noxious tasting agents are designed to deter chewing or sucking of the solid oral dosage form. Examples of suitable noxious tasting agents are:
  Denatonium benzoate
  Cayenne pepper
  Capsaicin Pharmaceutically Active Agents The invention features methods and compositions for immediate and extended release of pharmaceutically active agents using an ion exchange resin with benzonatate and one or more of the follow pharmaceutically active agents:

A: Anti-tussives, e.g., caramiphen edisylate, chlophedianol, codeine, dextromethorphan hydrobromide, hydrocodone, levopropoxyphene, morphine, codeine, ethylmorphine, dihydrocodeine, benzylmorphine, laudanum, dihydroisocodeine, nicocodeine, nicodicodeine, hydrocodone, hydromorphone, acetyldihydrocodeine, thebacon, diamorphine (heroin), acetylmorphine, noscapine, and pholcodine.

B: Narcotic analgesics, e.g., codeine, oxycodone, hydrocodone, diamorphine, pethidine, morphine, oxymorphone, nalorphine, naloxone, naltrexone, opium, hydromorphone, nicomorphine, dihydrocodeine, and papaveretum.

C: Decongestants, e.g., pseudoephedrine hydrochloride, phenylephrine bitartrate, and pseudoephedrine sulfate.

D: Non-steroidal anti-inflammatory drugs, e.g., aspirin, magnesium salicylate, diclofenac, etodolac, indometacin, nabumetone, sulindac, tolmetin, ibuprofen, ketoprofen, mefenamic acid, meclofenamic acid, phenylbutazone, piroxicam, meloxicam, celecoxib, parecoxib, rofecoxib, valdecoxib, and naproxen sodium.

E: Anti-emetic drugs, e.g., dolasetron, granisetron, ondansetron, tropisetron, palonosetron, mirtazapine, metoclopramide, cyclizine, diphenhydramine, dimenhydrinate, meclizine, promethazine, and hydroxyzine.

F: Anti-histamines, e.g., diphenhydramine, loratadine, desloratadine, meclizine, fexofenadine, pheniramine, cetirizine, promethazine, and chlorpheniramine.

G: Proton pump inhibitors (PPI), e.g., omeprazole, esomeprazole, pantoprazole, lansoprazole, and rabeprazole.

H: H2 Antagonists, e.g., cimetidine, ranitidine, and famotidine.

I: Anti-depressants, e.g., citalopram, escitalopram, fluoxetine, fluvoxamine, paroxetine, sertraline, desvenlafaxine, duloxetine, milnacipran, venlafaxine, atomoxetine, mazindol, reboxetine, viloxazine, amitriptyline, clomipramine, doxepin, imipramine, trimipramine, desipramine, nortriptyline, protriptyline, moclobemide, phenelzine, and selegiline.

J: Tranquilizers, e.g., amobarbital, pentobarbital, secobarbital, phenobarbital, clonazepam, diazepam, estazolam, flunitrazepam, lorazepam, midazolam, nitrazepam, oxazepam, triazolam, temazepam, chlordiazepoxide, and alprazolam.

K: Anti-convulsants, e.g., felbamate, carbamazepine, oxcarbazepine, vigabatrin, progabide, tiagabine, topiramate, gabapentin, pregabalin, ethotoin, and phenyloin.

L: Hypnotics, e.g., zolpidem, zaleplon, zopiclone, and eszopiclone.

M: Muscle relaxants, e.g., methocarbamol, carisoprodol, chlorzoxazone, cyclobenzaprine, gabapentin, metaxalone, and orphenadrine.

N: Anti-psychotics, e.g., haloperidol, droperidol, chlorpromazine, fluphenazine, perphenazine, prochlorperazine, thioridazine, trifluoperazine, mesoridazine, promazine, triflupromazine, levomepromazine, methotrimeprazine, pimozide, chlorprothixene, flupenthixol, thiothixene, zuclopenthixol, clozapine, olanzapine, risperidone, quetiapine, ziprasidone, amisulpride, asenapine, and paliperidone.

O: Anti-microbials, e.g., EDTA, zinc compounds, triclosan, domiphen, cetyl pyridium chloride, domiphen bromide, fluorides, alexidine, and octenidine.

P: Anti-diarrheals, e.g., bismuth subsalicylate and loperamide.

R: CNS stimulants, e.g., caffeine, cocaine, and amphetamines.

S: Attention Deficit and Hyperactivity Disorder drugs, e.g., methylphenidate, dextroamphetamine sulfate, amphetamine, and atomoxetine hydrochloride.

The invention also includes methods and compositions for delivering combinations of pharmaceutically active compounds. Examples of such combinations are:

A: benzonatate and an antihistamine
B: benzonatate and a decongestant
C: benzonatate and an analgesic
D: benzonatate and an NSAID
E: benzonatate and an antihistamine and a decongestant
F: benzonatate and an antihistamine and an analgesic
G: benzonatate and an antihistamine and an NSAID
H: benzonatate and an antihistamine and a decongestant and an analgesic Ion Exchange Resins The compositions of the invention include weak and strong acid ion exchange resins. Examples of suitable ion exchange resins are, for example, A: Amberlite IRP64 manufactured by DOW Chemical
B: DOWEX Mac-3 manufactured by DOW Chemical
C: Amberlite IRP69 manufactured by DOW Chemical
D: Dowex Marathon C, Dowex 88 and Dow XYS-40010 manufactured by Dow Chemical and the like.

Dosage Forms

Suitable dosage forms include tablets, capsules, orally disintegrating tablets, powders, beadlets, and the like.

EXAMPLES

One process to manufacture the weak and/or strong acid IER based products uses a modular approach in the preparation of the required intermediates. This allows maximal utilization of manufacturing capacity as well as minimizing material waste. The intermediate materials are used in the manufacture of the final dosage form. The flexibility of the intermediates when combined with commonly used excipients and the noxious tasting agent allows for an array of oral solid dosage forms. Two of the most commonly used in the art are outlined in the Examples.

Each of the compositions of the examples below is useful for oral administration as well as to prevent chewing of a solid oral dosage form of benzonatate.

Example 1

One thousand milligrams of IRP64 from Rohm and Haas (currently DOW) were added to deionized water (2.5 L) at room temperature. The resin and water were mixed using a magnetic stirring bar until a uniform suspension was obtained. 1,500 mg of benzonatate (from Toronto Reseach) was then added to the resin slurry and mixed in the primary vessel with continued mixing for a minimum of 4.0 hours to create the benzonatate resinate. The slurry was vacuum filtered to separate the drug resinate from the water. The resin particles were washed with 5-10 mls of deionized water. This process was repeated in order to generate adequate amounts of the benzonatate resinate to prepare the number of capsules required for dissolution testing. Care was taken to avoid cake formation by periodically mixing the resinate bed with a glass stirring rod. The resinate was then dried using a lab scale fluid bed dryer set at 55° C. inlet temperature. Drying was continued until a residual moisture content of 2.0% was obtained. Drug loading was tested and showed approximately 43% for IRP69 and 48% for IRP64 or approximately 43 mg of benzonatate per 100 mg of IRP 69 resinate and 48 mg of benzonatate per 100 mg of IRP64 resinate.

The dried resinate was then formulated into hard gelatin capsules using the materials in the examples listed in this section. The dried resinate was coated in a lab scale column coater using hydroxypropylmethylcellulose (HPMC) and triethyl citrate as a plasticizer. This is meant to enhance processing and protect the finished resin during subsequent capsule filling. The HPMC coating is a type which has no effect on the dissolution rate and is added as a processing aid to enhance material flow during additional manufacturing steps. The coated resin along with the remaining ingredients were blended in a lab scale diffusional mixer and filled into empty capsule shells.

The above method was repeated using a second ion exchange resin, IRP69 in place of the IRP64 but otherwise the details of the method were essentially identical. The table below shows the loading results for the two resins.

| Resin Loading Results | | |
| --- | --- | --- |
| RESIN | Loading (mg/mg) | Loading Efficiency |
| IRP69 | 0.425 | 69.7% |
| IRP64 | 0.480 | 87.9% |

The dissolution test used procedures devised by DOW Chemical using their proprietary, patent pending, buccal dissolution apparatus. There are a number of factors that are unique to characterizing buccal dissolution that do not apply to GI dissolution. They are:

Small volume
Short residence time
Solids transfer
Composition
Incomplete dissolution Most of the USP dissolution tests use large volumes of media-defined as 'sink conditions'; the aim is to get complete dissolution of the active ingredient. For buccal dissolution the volume of saliva is very small compared to that of the stomach and the residence time in the mouth is also very short, the bulk of the dosage form being swallowed within a minute.

In order for this test to give meaningful results it is necessary to use a dissolution media that simulates saliva. There is no USP recommended simulated saliva, so the composition used in these studies was based on published ranges. The composition used is shown below:

| KH2PO4 | 2 mM |
|---|---|
| NaCl | 40 mM |
| CaCl2 | 1.5 mM |
| NaOH | to pH 6.2 |

The technique uses a stirred flow-thru cell with a very short residence time.

Buccal dissolution studies were carried out with the above described neat benzonatate and benzonatate resonates. Dissolution data were obtained and these data are shown in FIG. 1. The plot shows the instantaneous concentration of benzonatate after initial dosage and flow of simulated saliva through the stirred cell. As can be seen in FIG. 1, both of the above benzonatate resinates showed a large reduction in buccal dissolution as compared to the neat benzonatate formulation. The IRP64 resinate produced a larger reduction in buccal benzonatate release than the IRP69 resinate Accordingly, a benzonatate solid oral dosage form created with an ion exchange resin would lead to a substantial reduction in exposure to benzonatate in the oral cavity and, accordingly, a reduction in the potential choking hazard associated with conventional liquid filled soft gel capsules.

Example 2

Mono-Substance IR Dosage Form, IRP64 Weak Acid Resin, Hard Gelatin Capsule

| Benzonatate IRP64 Resinate* (see Example 1) | 417 mg |
|---|---|
| Noxious tasting premix (denatonium benzoate) | 30 mg |
| Magnesium Stearate | 6 mg |
| Colloidal Silicon Dioxide | 6 mg |
| HPMC 6 cps | 12 mg |
| Talc | 6 mg |
| Triethyl Citrate | 6 mg |
| Empty Capsule Shell #00 | 118 mg |
| Total Dosage Form Weight | 601 mg |

*Equivalent to Benzonatate 200 mg.

Example 3

Mono-Substance IR Dosage Form, IRP64 Weak Acid Resin, Compressed Tablet

| Benzonatate IRP64 Resinate* (see Example 1) | 417 mg |
|---|---|
| Microcrystalline cellulose | 450 mg |
| Polyplasdone XL | 20 mg |
| Noxious tasting premix (denatonium benzoate) | 30 mg |
| HPMC 6 cps | 35 mg |
| Anhydrous lactose | 400 mg |
| Magnesium stearate | 6 mg |
| Total Dosage Form Weight | 1358 mg |

*Equivalent to Benzonatate 200 mg

Example 4

Mono-Substance IR Dosage Form, IRP 69 Strong Acid Resin, Hard Gelatin Capsule

| Benzonatate IRP69 Resinate* (see Example 1) | 465 mg |
|---|---|
| Noxious tasting premix (denatonium benzoate) | 30 mg |
| Magnesium Stearate | 6 mg |
| Colloidal Silicon Dioxide | 6 mg |
| HPMC 6cps | 12 mg |
| Talc | 6 mg |
| Triethyl Citrate | 6 mg |
| Empty Capsule Shell #00 | 118 mg |
| Total Dosage Form Weight | 649 mg |

*Equivalent to Benzonatate 200 mg.

Example 5

Mono-Substance IR Dosage Form, IRP 69 Strong Acid Resin, Compressed Tablet

| Benzonatate IRP69 Resinate* (see Example 1) | 465 mg |
|---|---|
| Microcrystalline cellulose | 450 mg |
| Polyplasdone XL | 20 mg |
| Noxious tasting premix (denatonium benzoate) | 30 mg |
| HPMC 6 cps | 35 mg |
| Anhydrous lactose | 400 mg |
| Magnesium stearate | 6 mg |
| Total Dosage Form Weight | 1406 mg |

*Equivalent to Benzonatate 200 mg

The process used in the preparation of the above single agent IR dosage forms are described diagrammatically in FIGS. 2, 3 6, 7 and 8. The processing for either dosage form uses an IR resin (strong and/or weak) coated intermediate, blended with dosage form specific excipients and a noxious tasting agent (e.g., those described above). The finished blend is tested and then used to form either the compressed tablet or the hard gelatin capsule dosage form.

Example 6

Fixed Combination Dosage Form Using the IR Component, IRP64 Weak Acid Resin

IR Mono-Substance with a Second Medicinal Agent, Hard Gelatin Capsule

| Benzonatate IRP64 Resinate* (see Example 1) | 417 mg |
|---|---|
| Pseudoephedrine HCl | 60 mg |

-continued

| | |
|---|---|
| Microcrystalline Cellulose | 425 mg |
| Polyvinylpyrrolidone | 35 mg |
| Noxious tasting premix (denatonium benzoate) | 30 mg |
| Magnesium Stearate | 6 mg |
| Colloidal Silicon Dioxide | 6 mg |
| Empty Capsule Shell #000 | 163 mg |
| HPMC 6 cps | 5 mg |
| Talc | 4 mg |
| Triethyl Citrate | 2 mg |
| Total Dosage Form Weight | 1153 mg |

*Equivalent to Benzonatate 200 mg

Example 7

IR Mono-Substance with a Second Medicinal Agent, Compressed Tablet

| | |
|---|---|
| Benzonatate IRP64 Resinate* (see Example 1) | 417 mg |
| Pseudoephedrine HCl | 60 mg |
| Microcrystalline Cellulose | 700 mg |
| Polyvinylpyrrolidone | 40 mg |
| Noxious tasting premix (denatonium benzoate) | 30 mg |
| Magnesium Stearate | 6 mg |
| Colloidal Silicon Dioxide | 6 mg |
| HPMC 6 cps | 40 mg |
| Total Dosage Form Weight | 1299 mg |

*Equivalent to Benzonatate 200 mg

Example 8

Fixed Combination Dosage Form Using the IR Component, IRP69 Strong Acid Resin IR Mono-Substance with a Second Medicinal Agent, Hard Gelatin Capsule

| | |
|---|---|
| Benzonatate IRP69 Resinate* (see Example 1) | 465 mg |
| Pseudoephedrine HCl | 60 mg |
| Microcrystalline Cellulose | 425 mg |
| Polyvinylpyrrolidone | 35 mg |
| Noxious tasting premix (denatonium benzoate) | 30 mg |
| Magnesium Stearate | 6 mg |
| Colloidal Silicon Dioxide | 6 mg |
| Empty Capsule Shell #000 | 163 mg |
| HPMC 6 cps | 5 mg |
| Talc | 4 mg |
| Triethyl Citrate | 2 mg |
| Total Dosage Form Weight | 1201 mg |

*Equivalent to Benzonatate 200 mg

Example 9

IR Mono-Substance with a Second Medicinal Agent, Compressed Tablet

| | |
|---|---|
| Benzonatate IRP69 Resinate* (see Example 1) | 465 mg |
| Pseudoephedrine HCl | 60 mg |
| Microcrystalline Cellulose | 700 mg |
| Polyvinylpyrrolidone | 40 mg |
| Noxious tasting premix (denatonium benzoate) | 30 mg |
| Magnesium Stearate | 6 mg |
| Colloidal Silicon Dioxide | 6 mg |
| HPMC 6 cps | 40 mg |
| Total Dosage Form Weight | 1347 mg |

*Equivalent to Benzonatate 200 mg

The process used in the preparation of these fixed combination dosage forms is described diagrammatically in FIGS. 2, 3, 5, 6, 9 and 10. The processing for either dosage form can use the same IR resin intermediate which has been coated. This IR resin-coated intermediate is blended with the noxious tasting agent and the dosage form specific excipients. The desired second pharmaceutically active agent intermediate is combined in a second blend along with the dosage form specific excipients. The finished blends are tested and then used to form either the compressed tablet or the hard gelatin capsule dosage form.

Example 9

Sustained Release (SR) Drug Delivery System Using the IR Mono-Substance Medicinal Agent, IRP69 Strong Acid Resin IR Mono-Substance Component Intermediate for Filling Hard Gelatin Capsules:

| | |
|---|---|
| Benzonatate IRP69 Resinate* (see Example 1) | 698 mg |
| Noxious tasting premix (denatonium benzoate) | 30 mg |
| Magnesium Stearate | 6 mg |
| Colloidal Silicon Dioxide | 6 mg |
| HPMC 6 cps | 7 mg |
| Talc | 6 mg |
| Triethyl Citrate | 6 mg |
| IR component weight | 759 mg |

*Equivalent to Benzonatate 300 mg

Example 10

Sustained Release (SR) Drug Delivery System Using the IR Mono-Substance Medicinal Agent, IRP64 Weak Acid Resin IR Mono-Substance Component Intermediate for Filling Hard Gelatin Capsules:

| | |
|---|---|
| Benzonatate IRP64 Resinate* (see Example 1) | 625 mg |
| Noxious tasting premix (denatonium benzoate) | 30 mg |
| Magnesium Stearate | 6 mg |

-continued

| | |
|---|---|
| Colloidal Silicon Dioxide | 6 mg |
| HPMC 6 cps | 7 mg |
| Talc | 6 mg |
| Triethyl Citrate | 6 mg |
| IR component weight | 686 mg |

*Equivalent to Benzonatate 300 mg

Example 11

SR Mono-Substance Component Intermediate for Filling Hard Gelatin Capsules

| | |
|---|---|
| IR Coated Benzonatate IRP69 Resinate* | 759 mg |
| Methacrylic Acid Copolymer | 40 mg |
| Talc | 4 mg |
| Triethyl Citrate | 6 mg |
| Colloidal Silicon Dioxide | 6 mg |
| Magnesium Stearate | 5 mg |
| SR component weight | 820 mg |

*Equivalent to Benzonatate 300 mg

Example 12

SR Mono-Substance Component Intermediate for Filling Hard Gelatin Capsules

| | |
|---|---|
| IR Coated Benzonatate IRP64 Resinate* | 686 mg |
| Methacrylic Acid Copolymer | 40 mg |
| Talc | 4 mg |
| Triethyl Citrate | 6 mg |
| Colloidal Silicon Dioxide | 6 mg |
| Magnesium Stearate | 5 mg |
| SR component weight | 747 mg |

*Equivalent to Benzonatate 300 mg

Example 13

IR/SR Encapsulation to Fill a Hard Gelatin Capsule to Deliver 600 mg

| | |
|---|---|
| IR component weight IRP69 | 759 mg |
| SR component weight IRP69 | 820 mg |
| Empty Capsule Shell #000 | 163 mg |
| Total Dosage Form Weight | 1742 mg* |

*Equivalent to Benzonatate 600 mg

Example 14

IR/SR Encapsulation to Fill Hard Gelatin Capsule to Deliver 600 mg

| | |
|---|---|
| IR component weight IRP64 | 686 mg |
| SR component weight IRP64 | 747 mg |
| Empty Capsule Shell #000 | 163 mg |
| Total Dosage Form Weight | 1596 mg* |

*Equivalent to Benzonatate 600 mg

The process used in the preparation of this extended release dosage form is described diagrammatically in FIGS. 3, 4, and 11. The IR resin-coated intermediate is blended with the dosage form specific excipients and the noxious tasting agent to form the IR component blend. A second portion of the IR resin coated intermediate is coated with an extended release polymer and then combined in a second blend along with the dosage form specific excipients. These are listed in the formulation section for each form. The finished blends are tested and then used to form the hard gelatin capsule extended release dosage form.

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

What is claimed is:

1. A solid oral dosage form of a pharmaceutical composition comprising benzonatate bound to at least one member of the group consisting of a strong acid ion exchange resin, a weak acid ion exchange resin and their combination to form a resinate; said solid oral dosage form additionally comprising a noxious tasting agent selected from the group consisting of denatonium benzoate, cayenne pepper, capsaicin and their combination; wherein said oral dosage form is useful for reducing or preventing adverse effects caused by the release of benzonatate into the oral cavity.

2. The solid oral dosage form of claim 1 comprising at least one additional pharmaceutically active agent.

3. The solid oral dosage form of claim 1, wherein at least two pharmaceutically active agents are bound to at least one ion exchange resin.

4. The solid oral dosage form according to claim 1, wherein said oral dosage form is useful for reducing or preventing sucking or chewing which may cause adverse effects caused by the release of benzonatate into the oral cavity.

5. A solid oral dosage form according to claim 1 comprising benzonatate bound to a weak acid ion exchange resin.

6. A solid oral dosage form according to claim 1 comprising benzonatate bound to a strong acid ion exchange resin.

7. A solid oral dosage form according to claim 1 comprising: (i) benzonatate bound to a strong acid ion exchange resin; and (ii) benzonatate bound to a weak acid ion exchange resin.

8. A solid oral dosage form of a pharmaceutical composition comprising: (i) benzonatate bound to a first ion exchange resin; (ii) benzonatate bound to a second ion exchange resin; wherein said first and second ion exchange resins are members of the group consisting of a strong acid ion exchange resin, a weak acid ion exchange resin and their combination; said solid oral dosage form additionally comprising a noxious tasting agent selected from the group consisting of denatonium benzoate, cayenne pepper, capsaicin and their combination; wherein said oral dosage form is useful for reducing or preventing adverse effects caused by the release of benzonatate into the oral cavity; and wherein said benzonatate bound second ion exchange resin is coated with an extended release coating.

9. A method of treating a cough while reducing or preventing adverse effects caused by a release of benzonatate into the oral cavity comprising treating a patient with a solid oral dosage form as described in claim 1.

10. A method of treating a cough while reducing or preventing adverse effects caused by a release of benzonatate into the oral cavity comprising treating a patient with a solid oral dosage form as described in claim 8.

* * * * *